(12) United States Patent
Felch et al.

(10) Patent No.: US 10,472,301 B2
(45) Date of Patent: *Nov. 12, 2019

(54) CATALYTIC SYSTEMS AND METHODS FOR PROCESS STREAM TREATMENT

(71) Applicant: Siemens Energy, Inc., Orlando, FL (US)

(72) Inventors: Chad L. Felch, Kronenwetter, WI (US); Matthew R. Patterson, Hatley, WI (US); Bryan J. Kumfer, Ringle, WI (US)

(73) Assignee: SIEMENS ENERGY, INC., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,749

(22) Filed: Jan. 30, 2019

(65) Prior Publication Data

US 2019/0152875 A1     May 23, 2019

Related U.S. Application Data

(63) Continuation of application No. 15/128,448, filed as application No. PCT/US2015/026357 on Apr. 17, 2015, now Pat. No. 10,246,382.

(Continued)

(51) Int. Cl.
*C02F 1/66* (2006.01)
*C02F 1/72* (2006.01)
(Continued)

(52) U.S. Cl.
CPC ............. *C07C 1/323* (2013.01); *C02F 1/725* (2013.01); *C02F 11/08* (2013.01); *C08L 33/26* (2013.01); *C10L 3/107* (2013.01); *C02F 1/66* (2013.01); *C02F 2101/32* (2013.01); *C02F 2101/36* (2013.01); *C02F 2101/38* (2013.01); (Continued)

(58) Field of Classification Search
CPC .. C02F 1/66; C02F 1/725; C02F 11/08; C02F 2101/32; C02F 2101/36; C02F 2101/38; C02F 2103/10; C02F 2103/28; C02F 2103/32; C02F 2103/365; C02F 2209/005; C02F 2209/06; C02F 2301/066; C02F 2303/18; C07C 1/323; C07C 2521/04;
(Continued)

(56) References Cited

U.S. PATENT DOCUMENTS

| 5,630,854 A * | 5/1997 | Sealock, Jr. | ............ C02F 1/025 48/127.7 |
| 2007/0210010 A1* | 9/2007 | Miyake | ...................... B01J 23/34 210/762 |
| 2013/0228528 A1 | 9/2013 | Felch | |

FOREIGN PATENT DOCUMENTS

| JP | H08192191 A | 7/1996 |
| JP | 2004300254 A * | 10/2004 |
| RU | 2498050 C2 | 11/2013 |

OTHER PUBLICATIONS

Machine translation of JP 2004-300254 A (2004) (obtained from Google Patent Apr. 2019) (Year: 2004).*

(Continued)

*Primary Examiner* — Lucas A Stelling

(57) ABSTRACT

Catalytic systems and methods for treating process streams are disclosed. Catalytic wet oxidation and hydrolysis techniques may be used to treat one or more undesirable constituents. Methane may be produced in connection with at least some embodiments.

17 Claims, 1 Drawing Sheet

Related U.S. Application Data

(60) Provisional application No. 61/981,272, filed on Apr. 18, 2014.

(51) Int. Cl.
| | |
|---|---|
| *C02F 11/08* | (2006.01) |
| *C07C 1/32* | (2006.01) |
| *C08L 33/26* | (2006.01) |
| *C10L 3/10* | (2006.01) |
| *C02F 101/32* | (2006.01) |
| *C02F 101/36* | (2006.01) |
| *C02F 103/28* | (2006.01) |
| *C02F 103/36* | (2006.01) |
| *C02F 101/38* | (2006.01) |
| *C02F 103/10* | (2006.01) |
| *C02F 103/32* | (2006.01) |

(52) U.S. Cl.
CPC ...... *C02F 2103/10* (2013.01); *C02F 2103/28* (2013.01); *C02F 2103/32* (2013.01); *C02F 2103/365* (2013.01); *C02F 2209/005* (2013.01); *C02F 2209/06* (2013.01); *C02F 2301/066* (2013.01); *C02F 2303/18* (2013.01); *C07C 2521/04* (2013.01); *C07C 2523/46* (2013.01); *C07C 2527/224* (2013.01); *C09K 2208/22* (2013.01)

(58) Field of Classification Search
CPC ........... C07C 2523/46; C07C 2527/224; C08L 33/26; C09K 2208/22; C10L 3/107
See application file for complete search history.

(56) References Cited

OTHER PUBLICATIONS

Ahmahdun et al., "Review of technologies for oil and gas produced water treatment" Journal of Hazardous Materials, 170 (2009) 530-551. (Year: 2009).*

Wikipedia; "Kinetic Inhibitor"; [online], Nov. 2013 <URL:https://en.wikipedia.org/w/index.php?title=Kinetic_Inhibitor&oldid=580132795>.

Nakarit, Chittawan, "Gas Hydrate Formation and Control by the Use of Chemicals", University of Tavanger, Faculty of Science and Technology Department of Mathematics and Natural Science, Jun. 2012, pp. 1-67.

Ke, Wei et al, "Kinetic Hydrate Inhibitor Studies for Gas Hydrate Systems: A Review of Experimental Equipment and Test Methods", Energy & Fuels vol. 30, DOI: 10.1021/acs.energyfuels.6b02739, Nov. 22, 2016, pp. 10015-10028.

* cited by examiner

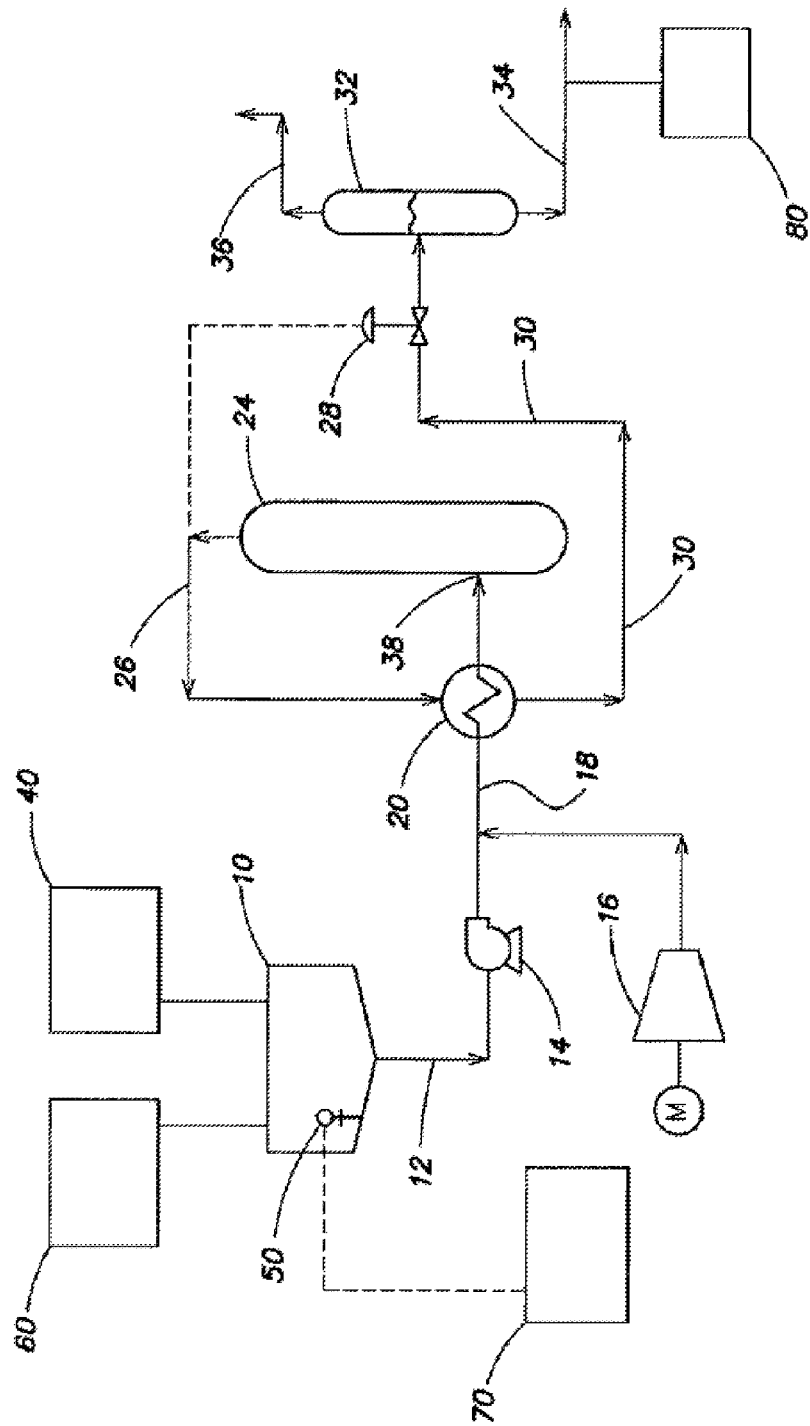

CATALYTIC SYSTEMS AND METHODS FOR PROCESS STREAM TREATMENT

CROSS-REFERENCE TO RELATED APPLICAITONS

This application is a continuation of U.S. patent application Ser. No. 15/128,448, filed Sep. 23, 2016, which was a National Stage Application of PCT/US2015/026357, filed Apr. 17, 2015, which claimed priority to U.S. Provisional Application No. 61/981,272, filed Apr. 18, 2014. The entirety of each application is hereby incorporated by reference.

BACKGROUND

Field of the Invention

The present invention relates generally to the treatment of process streams and, more particularly, to catalytic wet oxidation and hydrolysis systems and methods for the treatment of undesirable constituents therein.

Description of Related Art

To meet energy and manufacturing needs, oil and gas are routinely extracted from underground sources. Conventional oil and gas extraction is a water intensive process. Produced water is typically unfit for discharge into local water sources and may be injected into underground wells for disposal. Alternatively, produced water may be treated to render it suitable for a variety of uses.

In a conventional oil or gas extraction operation, injected water may be used to drive oil or gas to the surface at a well head. The injected water and/or the existing water in the formation surfaces as a mixture, or emulsion, known as "produced water" that includes the oil and gas products. The water portion and oil portion of the produced water are separated by various unit operations. Portions of the separated water stream may undergo different treatment operations depending on their intended use. Intended uses of the water stream may include reinjection to permanent well disposal or waterflooding. Alternatively, the intended use may require an improved water quality, such as for irrigation.

Characteristics and components of the produced water may be detrimental to the piping system carrying it. For example, in the context of deep well applications, in colder temperatures organics from the produced water form organic ice (hydrates) on the walls of pipes carrying produced water, particularly where there are large pressure drops.

The problem of organic ice has in the past been addressed through the addition of glycols to the produced water, however that process is expensive and requires relatively high concentrations of glycols to be effective. Furthermore, the glycols must subsequently be removed, adding an additional step to the overall treatment process.

Kinetic hydrate inhibitors "KHIs" (also known as "LDHI", low dose hydrate inhibitors) serve as an alternative to glycols for inhibiting icing, where they can be introduced in lower concentrations.

While KHIs enjoy certain advantages over glycols they also have disadvantages. For example, KHIs have a cloud point generally in the range of 40-80° C.

A produced water solution in that temperature range may become cloudy from precipitation of KHI. Some regulatory bodies fear that such a cloudy solution could plug off reservoirs and have therefore banned deep well reinjection of produced waters containing KHI. As a result their use in such applications has been limited.

KHI is a class of high weight organic polymers. KHI share some similar properties to another class of high weight polymers present in certain produced waters—HPAM (hydrolyzed polyacrylamide). HPAM increases viscosity to help remove oil from underground often as part of a more general process referred to as enhanced oil recovery (EOR). The increased viscosity created by the HPAM to aid in oil or gas removal subsequently becomes an impediment to separation processes applied to the produced water, at it forms emulsions that are difficult to separate. As a result, HPAM is preferably removed at some stage during produced water treatment to reduce the viscosity of the stream and aid in separation.

KHI and HPAM each contribute to the chemical oxygen demand (COD) of produced water. Other sources of COD in produced water include light hydrocarbons and other organics.

SUMMARY

In accordance with one or more aspects, a method of treating an aqueous mixture is provided. The method may comprise: introducing an aqueous mixture comprising at least one of KHI and HPAM to a treatment vessel; subjecting the aqueous mixture to a superatmospheric pressure in or upstream of the treatment vessel; subjecting the aqueous mixture to an elevated temperature in or upstream of the treatment vessel; introducing a catalyst to the aqueous mixture in or upstream of the treatment vessel; contacting the catalyst with the aqueous mixture for a sufficient time to disrupt chemical bonds in at least a portion of the at least one of KHI and HPAM; and separating the disrupted portion of the at least one of KHI and HPAM from the aqueous mixture to produce a treated aqueous mixture having a residual level of the at least one of KHI and HPAM below a predetermined threshold.

In accordance with one or more aspects, the method may further comprise introducing a pressurized oxygen-rich gas to the aqueous mixture upstream of the treatment vessel. Subjecting the aqueous mixture in the treatment vessel to a superatmospheric pressure may comprise charging the pressure vessel with an oxygen-poor gas. The oxygen-poor gas may be an inert gas.

The inert gas may comprise nitrogen. The catalyst may comprise a heterogeneous catalyst. The heterogeneous catalyst may comprise ruthenium. Contacting the catalyst with the aqueous mixture may facilitate hydrolysis of at least a portion of the at least one of KHI and HPAM. Contacting the catalyst with the aqueous mixture may facilitate oxidation of at least a portion of the at least one of KHI and HPAM. The method may further comprise injecting the treated aqueous mixture underground. The aqueous mixture may comprise KHI and the predetermined threshold may be 100 mg/l. The aqueous mixture may comprise HPAM and the predetermined threshold may be 100 mg/l. The elevated temperature may be at least about 250° C. The superatmospheric pressure may be between 20 ATM and 240 ATM. The aqueous mixture may be a produced water or derived from a produced water. The produced water may be formed by an enhanced oil recovery process.

In accordance with one or more aspects, a method of treating produced water is provided. The method may comprise: introducing a produced water comprising a chemical oxygen demand of at least 30,000 mg/L to a treatment vessel; subjecting the produced water to a superatmospheric pressure in or upstream of the treatment vessel; subjecting the produced water to an elevated temperature in or upstream of the treatment vessel; introducing a catalyst to the treatment vessel; contacting the catalyst with the produced water for a sufficient time to disrupt chemical bonds in at least a portion of constituents contributing to the chemical oxygen demand; and separating the disrupted portion of constituents contributing to the chemical oxygen demand from the produced water to produce a treated produced water having a chemical oxygen demand below a predetermined threshold.

In accordance with one or more aspects, the predetermined threshold for chemical oxygen demand may be about 100 mg/L. The produced water may comprise at least one of KHI and HPAM. The method may further comprise introducing a pressurized oxygen-rich gas to the produced water upstream of the treatment vessel. The catalyst may comprise a heterogeneous catalyst. The heterogeneous catalyst may comprise ruthenium. Contacting the catalyst with the aqueous mixture may facilitate hydrolysis of at least a portion of the constituents contributing to the chemical oxygen demand. Contacting the catalyst with the aqueous mixture may facilitate oxidation of at least a portion of the constituents contributing to the chemical oxygen demand.

In accordance with one or more aspects, a method of producing methane is disclosed. The method may comprise: introducing a produced water comprising a chemical oxygen demand of at least 30,000 mg/L to a treatment vessel; subjecting the produced water to a pressure from about 20 ATM to about 240 ATM in or upstream of the treatment vessel; subjecting the produced water to a temperature from about 150° C. to about 373° C. in or upstream of the treatment vessel; introducing a catalyst to the produced water in or upstream of the treatment vessel to promote methane formation; and capturing the formed methane.

In accordance with one or more aspects, the method may further comprise introducing a pressurized oxygen-rich gas to the produced water upstream of the treatment vessel. The catalyst may comprise a heterogeneous catalyst. The heterogeneous catalyst may comprise ruthenium. Contacting the catalyst with the aqueous mixture may facilitate hydrolysis of at least a portion of the constituents contributing to the chemical oxygen demand. Contacting the catalyst with the aqueous mixture may facilitate oxidation of at least a portion of the constituents contributing to the chemical oxygen demand. The method may further comprise delivering the captured methane to a point of use.

BRIEF DESCRIPTION OF THE DRAWINGS

The accompanying drawings are not intended to be drawn to scale. In the drawings, each identical or nearly identical component that is illustrated in various figures is represented by like numeral. For purposes of clarity, not every component may be labeled in every drawing. Preferred, non-limiting embodiments will be described with reference to the accompanying drawings, in which:

FIG. 1 is a system diagram of a treatment system according to one or more embodiments.

DETAILED DESCRIPTION

This invention is not limited in its application to the details of construction and the arrangement of components as set forth in the following description or illustrated in the drawings. The invention is capable of embodiments and of being practiced or carried out in various ways beyond those exemplarily presented herein.

Wet oxidation is a technology for treating process streams. The method involves aqueous phase oxidation of undesirable constituents by an oxidizing agent, generally molecular oxygen from an oxygen-rich gas, at elevated temperatures and pressures. The process can convert organic contaminants to carbon dioxide, water and biodegradable short chain organic acids, such as acetic acid. Inorganic constituents including sulfides, mercaptides and cyanides can also be oxidized.

Hydrolysis is a process similar to the wet air oxidation process for the treatment of wastewaters when oxygen is not a necessary reactant. In hydrolysis, certain constituents of wastewaters and sludges can react directly with water at elevated temperatures and pressures to yield a treated effluent that is detoxified or meets the desired treatment objective.

In catalytic wet oxidation or hydrolysis processes an aqueous stream to be treated is mixed with an oxidizing agent (or not, in the case of hydrolysis) and contacted with a catalyst at elevated temperatures and pressures. Heterogeneous catalysts typically reside on a bed over which the aqueous mixture is passed, or in the form of solid particulate which is blended with the aqueous mixture prior to oxidation or hydrolysis. The catalyst may be filtered out of the effluent downstream of the reactor unit. The catalytic material may either be recycled or removed and replaced.

In accordance with one or more embodiments, one or more systems and methods for treating process streams are disclosed. In typical operation, the disclosed systems may receive process streams from community, industrial, gas/oil production, or residential sources. For example, in embodiments in which the system is treating wastewater, the process stream may be delivered from a municipal wastewater sludge or other large-scale sewage system. Process streams may also originate, for example, from food processing plants, chemical processing facilities, gasification projects, or pulp and paper plants. Process streams may also originate from the fluid mixtures used to extract oil and gas from underground sources. Thus, the process stream may include at least a small amount of hydrocarbons. The process stream may be moved through the system by an operation upstream or downstream of the system.

As used herein, the term "process stream" refers to an aqueous mixture deliverable to the system for treatment. After treatment, the process stream may be further processed, returned to an upstream process, deep well injected, or may otherwise exit the system as waste. The aqueous mixture typically includes at least one undesirable constituent capable of being oxidized or hydrolysized. The undesirable constituent may be any material or compound targeted to be removed from the aqueous mixture, such as for public health, process design and/or aesthetic considerations. In some embodiments, the undesirable constituents capable of being oxidized or hydrolysized are organic compounds. Certain large organic polymers, for example, KHI, HPAM, large amine compounds, and related species can also be oxidized or hydrolysized, so that they may be broken down into smaller components, for example, monomers. A source of an aqueous mixture to be treated by the system, such as a slurry, may take the form of direct piping from a plant or holding vessel. In some embodiments, the aqueous mixture may have a concentration of the above-described large organic polymers in a range from a few ppm to about 5%.

In accordance with one or more embodiments, it may be desirable to disrupt one or more specific chemical bonds in the undesirable constituent or degradation product(s) thereof. An oxidation reaction is one destruction technique, capable of converting oxidizable organic contaminants to carbon dioxide, water and biodegradable short chain organic acids, such as acetic acid. One or more disclosed embodiments involve systems and methods for oxidative treatment of aqueous mixtures containing one or more undesirable constituents.

In one embodiment, an aqueous mixture including at least one undesirable constituent is wet oxidized. The aqueous mixture is oxidized with an oxidizing agent at an elevated temperature and superatmospheric pressure for a duration sufficient to treat the at least one undesirable constituent. The oxidation reaction may substantially destroy the integrity of one or more chemical bonds in the undesirable constituent. As used herein, the phrase "substantially destroy" is defined as at least about 95% destruction. The process of the present invention is generally applicable to the treatment of any undesirable constituent capable of being oxidized or hydrolysized.

It was unexpectedly found that catalytic wet air oxidation systems and hydrolysis systems may be incorporated in processes for removing large polymeric species, such as KHI and HPAM from a produced water, since WAO and hydrolysis have been classically used in downstream operations rather that upstream applications such as discussed herein.

According to one or more embodiments, an aqueous mixture, such as a produced water stream, may be subjected to catalytic treatment. The method may include increasing the pressure and temperature of a produced water comprising KHI and/or HPAM. The method may include introducing a catalyst to the treatment stream. In a wet air oxidation system, an oxygen-rich gas is introduced to the stream. The produced water is then treated in a reactor, where it is in contact with the catalyst to promote oxidation and/or hydrolysis. During treatment, chemical bonds in at least a portion of the KHI and/or HPAM are disrupted through oxidation and/or hydrolysis, to produce a transformed or broken down product. KHI and HPAM are each large polymers that contribute to an increased viscosity of the produced water which interferes with separation processes. By breaking down these large components into smaller components, for example, monomers, separation processes are thereby facilitated. The disrupted unwanted components are separated from the stream to produce a treated aqueous mixture having a residual level of KHI and/or HPAM below a predetermined threshold such as may be dictated by a relevant regulatory agency or otherwise sufficient to alleviate issues in water treatment such as cloud point, viscosity, or emulsions. For example, the predetermined threshold may be about 100 mg/l in some non-limiting embodiments. The predetermined threshold may be associated with a level sufficient to remove or address one or more undesirable characteristics or properties.

A variety of approaches are available to determine whether the residual levels of the unwanted components are below a desired level in accordance with one or more embodiments. One approach is to base the determination on a COD measurement. This approach is available where the unwanted species may be safely presumed to constitute a large share of the COD value, as is the case with produced water at this stage of its treatment cycle, and therefore COD may be understood as a proxy value for the KHI or HPAM value. Under these circumstances, if COD is reduced by a certain percentage, or below a certain value, then, by proxy the residual KHI or HPAM is below a predetermined threshold.

An alternative approach is to apply analytical techniques such as size exclusion chromatography ("SEC") to determine if the unwanted constituent is below a predetermined threshold. SEC separates molecules according to their size and therefore may be used to determine a concentration of all molecules above a certain size. Because KHI and HPAM are relatively large polymers, in a produced water stream, KHI or HPAM may constitute the bulk of molecules above a certain size. The concentration of large molecules determined through SEC may therefore be a serviceable estimation for the concentration of residual KHI or HPAM. Other techniques may also be applied to determine if the residual KHI or HPAM is below a predetermined threshold.

In addition to removing unwanted species, application of catalytic wet air oxidation or hydrolysis on a produced water stream may have the added benefit of methane generation in accordance with one or more embodiments, which may be subsequently captured and used or sold as a byproduct. Methane generation may be facilitated by use of catalyst, and is especially abundant where fresh catalyst material is present. Methane generation may result from carbonaceous material in the stream undergoing a Fischer-Tropsch process.

The disclosed wet oxidation or hydrolysis processes may be performed in any known batch or continuous unit suitable for the compounds to be treated. Typically, aqueous phase oxidation is performed in a continuous flow wet oxidation system, as exemplarily shown in FIG. 1. Any oxidizing agent may be used. The oxidant is usually an oxygen-containing gas, such as air, oxygen-enriched air, or essentially pure oxygen. As used herein, the phrase "oxygen-enriched air" is defined as air having an oxygen content greater than about 21%. Aspects of the operation of the hydrolysis system may be similar to those of the wet air oxidation system 5 described with reference to FIG. 1. A hydrolysis system, however, would not need to include a compressor 16 as described below. In some embodiments, pre-treatment may be performed such as but not limited to gravity separation, filtration, and/or dissolved/induced gas floatation.

In typical operation of wet oxidation system 5, and with reference to FIG. 1, an aqueous mixture from a source, shown as storage tank 10, flows through a conduit 12 to a high pressure pump 14 which pressurizes the aqueous mixture. The aqueous mixture may be pressurized by charging the vessel with an inert gas. In some embodiments, the inert gas may have an oxygen content less than air (otherwise referred to as oxygen-poor), such as nitrogen. The aqueous mixture is mixed with a pressurized oxygen-containing gas, supplied by a compressor 16, within a conduit 18. The oxygen-containing gas may be an oxygen-rich gas, one having an oxygen content greater than air. The aqueous mixture flows through a heat exchanger 20 where it is heated to a temperature which initiates oxidation. The heated feed mixture then enters a reactor vessel 24 at inlet 38. The wet oxidation reactions are generally exothermic and the heat of reaction generated in the reactor may further raise the temperature of the mixture to a desired value. The bulk of the oxidation reaction occurs within reactor vessel 24 which provides a residence time sufficient to achieve the desired degree of oxidation. The oxidized aqueous mixture and oxygen depleted gas mixture then exit the reactor through a conduit 26 controlled by a pressure control valve 28. The depleted gas mixture may comprise, for example, $H_2$, $CO_2$, and other entrained volatile vapors. The hot oxidized effluent traverses the heat exchanger 20 where it is cooled against incoming raw aqueous mixture and gas mixture. The cooled effluent mixture flows through a conduit 30 to a separator vessel 32 where liquid and gases are separated. The liquid effluent exits the separator vessel 32 through a lower conduit 34 while off gases are vented through an upper conduit 36. Treatment of the off gas may be required in a downstream off gas treatment unit depending on its composition and the requirements for discharge to the atmosphere. The wet oxidized effluent may typically be discharged into a separate operations unit for further treatment. The effluent may also be recycled for further processing by the wet oxidation system.

A catalyst may be added to the aqueous mixture at any point in the wet oxidation system. The catalyst may be mixed with the aqueous mixture. In one embodiment, the catalyst may be added to the source of the aqueous mixture feeding the wet oxidation unit as illustrated in FIG. 1 in which catalyst source 40 is fluidly connected to storage tank 10. In some embodiments, the catalyst may be directly added to the wet oxidation unit. In other embodiments, the catalyst may also be supplied to the aqueous mixture prior to heating and/or pressurization.

In yet other embodiments, the catalyst may already be present in the process stream to be treated. The aqueous mixture supplied to the oxidation unit may contain a catalytic material. For example, transition metals may be present in a waste stream to be treated by the catalytic wet oxidation system. Aqueous slurries, such as those containing volatile organic carbons, may contain metals capable of acting as a catalyst. For example, the aqueous mixture may be a slurry of gasification byproducts.

In some embodiments, the system may include a controller 70 for adjusting or regulating at least one operating parameter of the system or a component of the system, such as, but not limited to, actuating valves and pumps. Controller 70 may be in electronic communication with sensor 50 as illustrated in FIG. 1. Controller 70 may be generally configured to generate a control signal to adjust the pH level of the aqueous mixture in response to the pH sensor 50 registering a pH level outside a predetermined pH range. For example, controller 70 may provide a control signal to one or more valves associated with pH adjuster source 60 to add pH adjuster to aqueous mixture source 10. In some embodiments, adjusting the pH level may help the hydrolysis or oxidation of polymers. In at least some embodiments, a neutral pH level may be avoided in favor of either an alkaline or acidic environment.

The controller 70 is typically a microprocessor-based device, such as a programmable logic controller (PLC) or a distributed control system, that receives or sends input and output signals to and from components of the wet oxidation system. Communication networks may permit any sensor or signal-generating device to be located at a significant distance from the controller 70 or an associated computer system, while still providing data therebetween. Such communication mechanisms may be effected by utilizing any suitable technique including but not limited to those utilizing wireless protocols.

According to one or more embodiments, the wet oxidized liquid effluent stream may be processed by a secondary treatment unit 80 connected downstream of the oxidation reactor vessel 24 to remove remaining undesirable constituents present and/or polish when necessitated or desired. The secondary treatment unit 80 may be a chemical scrubber, a biological scrubber, an adsorption media bed, or other unit operation for separation. The secondary treatment unit 80 may be sized to provide a surface area consistent with the desired degree of polishing. Alternatively, the liquid effluent may also be recycled back to reactor vessel 24 for further processing. Treatment of the off gas may also be required in a downstream off gas treatment unit depending on its composition and the requirements for discharge to the atmosphere.

Sensors to detect a concentration of a targeted constituent may be provided upstream and/or downstream of the wet oxidation unit 24 to facilitate system control. For example, a sensor may be positioned at conduit 26 and be in communication with controller 70 to determine and/or control whether the liquid effluent stream should be diverted to the secondary treatment unit 80 to meet established environmental regulations.

Sufficient oxygen-containing gas is typically supplied to the system to maintain residual oxygen in the wet oxidation system off gas, and the superatmospheric gas pressure is typically sufficient to maintain water in the liquid phase at the selected oxidation temperature. For example, the minimum system pressure at 240° C. is 33 atmospheres, the minimum pressure at 280° C. is 64 atmospheres, and the minimum pressure at 373° C. is 215 atmospheres. In one embodiment, the aqueous mixture is oxidized at a pressure of about 30 atmospheres to about 275 atmospheres. The wet oxidation process may be operated at an elevated temperature below 374° C., the critical temperature of water. In some embodiments, the wet oxidation process may be operated at a supercritical elevated temperature. The retention time for the aqueous mixture within the reaction chamber should be generally sufficient to achieve the desired degree of oxidation. In some embodiments, the retention time is above about one hour and up to about eight hours. In at least one embodiment, the retention time is at least about 15 minutes and up to about 6 hours. In one embodiment, the aqueous mixture is oxidized for about 15 minutes to about 4 hours. In another embodiment, the aqueous mixture is oxidized for about 30 minutes to about 3 hours. In at least some embodiments, produced water may be exposed to a heterogeneous catalyst in a pressure vessel at an elevated temperature and pressure for a sufficient time to catalytically react with KHI and/or HPAM to reduce a COD level of the produced water while generating methane as a byproduct.

According to one or more embodiments, the wet oxidation or hydrolysis process is a catalytic wet oxidation process. Any oxidation reaction may be mediated by a catalyst. The aqueous mixture containing at least one undesirable constituent to be treated is generally contacted with a catalyst and an oxidizing agent at an elevated temperature and superatmospheric pressure. An effective amount of catalyst may be generally sufficient to increase reaction rates and/or improve the overall destruction removal efficiency of the system, including enhanced reduction of chemical oxygen demand (COD) and/or total organic carbon (TOC). The catalyst may also serve to lower the overall energy requirements of the wet oxidation system.

In at least one embodiment, the catalyst may be a metal or metal alloy. In one or more embodiments, for example, the catalyst may be ruthenium, nickel, cobalt, iron or alloys or mixtures thereof. In some embodiments, a catalyst may be selected based on a characteristic of the aqueous mixture. The heterogeneous catalyst may be supplied on a support. The support may be, for example, an alumina, silica, or silicon carbide support.

As discussed above with respect to typical operation of the oxidation unit, a liquid effluent is separated from the oxidized aqueous mixture downstream of the oxidation reactor. In some embodiments, the catalyst may be recovered from the liquid effluent by a separation process. For example, in some embodiments the catalyst may be precipitated out of the effluent stream. In one embodiment, a crystallizer may be used to recover the catalyst. The catalyst may then be recycled back to the wet oxidation system or removed and replaced with fresh catalyst.

It should be appreciated that numerous alterations, modifications and improvements may be made to the illustrated systems and methods. For example, one or more systems may be connected to multiple sources of process streams. In some embodiments, the wet oxidation system may include additional sensors for measuring other properties or operating conditions of the system. For example, the system may include sensors for temperature, pressure drop, and flow rate at different points to facilitate system monitoring. In accordance with one or more embodiments, the catalyst may be replenished during the wet oxidation process.

The invention contemplates the modification of existing facilities to retrofit one or more systems or components in order to implement the techniques of the invention. An existing wet oxidation system can be modified in accordance with one or more embodiments exemplarily discussed herein utilizing at least some of the preexisting equipment. For example, one or more pH sensors may be provided and a controller in accordance with one or more embodiments presented herein may be implemented in a preexisting wet oxidation system to promote catalyst solubility, such as when a homogenous catalyst such as copper is used. According to other embodiments, pH may be controlled to keep the catalyst insoluble, for example, when a heterogeneous catalyst is used such as a cerium catalyst on a support.

The function and advantages of these and other embodiments of the present invention will be more fully understood from the following examples. These examples are intended to be illustrative in nature and are not considered to be limiting the scope of the invention. In the following examples, compounds are treated by wet oxidation or hydrolysis to effect destruction of bonds therein.

EXAMPLES

Example One

Four samples of a produced water containing KHI were subjected to wet air oxidation under various conditions. The results are shown in Table 1.

In all four samples the temperature of the produced water was 250° C. within the reactor. The average residence times, charge pressure, and charge gas are all shown in Table 1. In each case ruthenium was used as the catalyst. The ruthenium was supported on either alumina or silicon carbide, as shown in Table 1. The measured COD of the feed produced water stream was 23.1 g/l.

It was observed that when heterogeneous catalyst was present, methane, a valuable and unexpected byproduct, formed during process start up. Catalytic treatment further resulted in a reduction of COD of up to 59.7%, indicating significant treatment of KHI.

TABLE 1

Results of Testing on a First Produced Water:

| | Feed | Sample 1 | Sample 2 | Sample 3 | Sample 4 |
|---|---|---|---|---|---|
| Temperature, ° C. | — | 250 | 250 | 250 | 250 |
| Residence Time, min | — | 15 | 15 | 180 | 180 |
| Charge Pressure, psig | — | 300 | 300 | 600 | 600 |
| Charge Gas | — | Air | Nitrogen | Nitrogen | Nitrogen |
| Catalyst | — | Ru on Alumina | Ru on Alumina | Ru on SiC (silicon carbide) | Ru on Alumina |
| COD, g/l | 23.1 | 10.6 | 15.8 | 10.4 | 9.3 |
| TOC, g/l | — | 3.1 | 4.8 | 3.08 | 2.7 |
| % Methane in Off Gas | — | 2.7 | 3.7 | 4.7 | 5.3 |
| % COD Reduction | — | 54.1 | 31.6 | 55.0 | 59.7 |

Example Two

Two samples of a produced water containing KHI were subjected to wet air oxidation treatment under varying conditions. The results are shown in Table 2.

In the first sample no catalyst was present. This sample experienced no methane production and limited COD reduction. In the second sample, ruthenium on alumina was used as the catalyst. In the second sample significant methane gas production and COD reduction were observed, indicative of the value of a catalyst in the process.

TABLE 2

Results of Testing on a Second Produced Water

| | Feed | Sample 1 | Sample 2 |
|---|---|---|---|
| Temperature, ° C. | — | 250 | 250 |
| Residence Time, min | — | 180 | 180 |
| Charge Pressure, psig | — | 600 | 600 |
| Charge Gas | — | Nitrogen | Nitrogen |
| Catalyst | — | None | Ru on Alumina |
| COD, g/l | 13.8 | 13.1 | 2.91 |
| TOC, g/l | — | 3.65 | 0.64 |
| % Methane in Off Gas | — | 0.0 | 5.3 |
| % COD Reduction | — | 5.1 | 78.9 |

Example Three

A produced water containing 15 g/l of KHI was subjected to hydrolysis treatment under varying conditions, without introducing an oxygen-rich gas to the stream to be treated. The conditions and testing results for each of the four different sample treatment streams are shown in Table 3. Size exclusion chromatography analysis was performed to estimate KHI presence in both the feed and the effluent.

In the first and third samples no catalyst was present. Each of these samples resulted in minimal COD reduction. These samples also experienced almost no methane production.

In the second and fourth samples, ruthenium on alumina was used as the catalyst. In the second sample, treatment was carried out at 200° C. In the fourth sample, treatment was carried out at 260° C.

In the second sample, where treatment was carried out at 200° C., very little methane was produced. Furthermore, COD reduction improved over samples where no catalyst was present, but was still relatively low. The second sample resulted in a 31.6% reduction in HKI.

In the fourth sample, however, where treatment was carried out at 260° C., a significant percentage of the off gas was in the form of methane, a valuable by-product. Furthermore, sample 4 experienced a 49% reduction in COD and a 54.64% reduction in KHI.

These results demonstrate that under proper conditions significant KHI and COD reduction may be achieved through the disclosed method along with methane production.

TABLE 3

Results of testing on a third produced water.

|  | Feed | Sample 1 | Sample 2 | Sample 3 | Sample 4 |
| --- | --- | --- | --- | --- | --- |
| Temperature, ° C. | — | 200 | 200 | 260 | 260 |
| Residence Time, min | — | 15 | 15 | 15 | 15 |
| Charge Pressure, psig | — | 300 | 300 | 300 | 300 |
| Charge Gas | — | Nitrogen | Nitrogen | Nitrogen | Nitrogen |
| Catalyst | — | None | 2% Ru/Alumina | None | 2% Ru/Alumina |
| COD, g/l | 29.8 | 29.9 | 27.2 | 28.8 | 15.2 |
| TOC, g/l | 7.05 | 8.22 | 7.85 | 8.16 | 4.24 |
| KHI, g/l | 15.19 | 12.62 | 10.39 | 13.79 | 6.89 |
| % KHI Reduction | — | 16.92 | 31.6 | 9.2 | 54.64 |
| % Methane in Off Gas | — | <0.01 | 0.01 | <0.01 | 8.42 |
| % COD Reduction | — | −0.3 | 8.7 | 3.4 | 49 |

Example Four

A produced water containing 1.88 g/l of HPAM in the form of Superfloc® flocculant commercially available from Cytec, Inc. was subjected to hydrolysis treatment under varying conditions, without introducing an oxygen-rich gas to the stream to be treated. The conditions and testing results for each of the four different sample treatment streams are shown in Table 4. In the first and third samples no catalyst was present.

In the second and fourth samples, ruthenium on alumina was used as the catalyst. In the second sample, treatment was carried out at 200° C. In the fourth sample, treatment was carried out at 260° C.

Samples 2 and 4, where catalyst was present, showed a greater reduction in COD and TOC than in samples 1 and 3, where no catalyst was present. In each of the samples where catalyst was present a greater than 50% reduction of COD was achieved.

TABLE 4

Results of testing on a fourth produced water.

|  | Feed | Sample 1 | Sample 2 | Sample 3 | Sample 4 |
| --- | --- | --- | --- | --- | --- |
| Temperature, ° C. | — | 200 | 200 | 260 | 260 |
| Residence Time, min | — | 15 | 15 | 15 | 15 |
| Charge Pressure, psig | — | 300 | 300 | 300 | 300 |
| Charge Gas | — | Nitrogen | Nitrogen | Nitrogen | Nitrogen |
| Catalyst | — | None | 2% Ru/Alumina | None | 2% Ru/Alumina |
| COD, g/l | 2.0 | 1.02 | 0.89 | 1.07 | 0.78 |

TABLE 4-continued

Results of testing on a fourth produced water.

|  | Feed | Sample 1 | Sample 2 | Sample 3 | Sample 4 |
| --- | --- | --- | --- | --- | --- |
| TOC, g/l | 0.51 | 0.414 | 0.378 | 0.452 | 0.201 |
| % Methane in Off Gas | — | <0.01 | 0.01 | <0.01 | 0.4 |
| % COD Reduction | — | 49.0 | 55.5 | 46.5 | 61.1 |

Having now described some illustrative embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

It is to be appreciated that embodiments of the devices, systems and methods discussed herein are not limited in application to the details of construction and the arrangement of components set forth in the description or illustrated in the accompanying drawings. The devices, systems and methods are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto the invention may be practiced otherwise than as specifically described.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element, nor the order of elements presented, does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of producing methane comprising:
contacting an aqueous fluid comprising at least one organic compound comprising at least one of a kinetic hydrate inhibitor and a hydrolyzed polyacrylamide with a heterogeneous catalyst at a pressure from about 20 atm to about 240 atm and a temperature from about 150° C. to about 373° C. to hydrolyze the at least one organic compound in the fluid and generate an amount of methane,
wherein the heterogeneous catalyst comprises a member selected from the group consisting of ruthenium, nickel, cobalt, iron, and combinations thereof, and a solid support selected from the group consisting of alumina, silica, and a carbide.

2. The method of claim 1, wherein the pressure is from about 20 atm to about 40 atm.

3. The method of claim 1, wherein the temperature is from about 200° C. to about 260° C.

4. The method of claim 1, wherein the aqueous fluid comprises produced water.

5. The method of claim 1, wherein the heterogeneous catalyst comprises ruthenium.

6. The method of claim 1, wherein the contacting is done in a treatment vessel, wherein the method further comprises introducing a pressurized oxygen-rich gas to the aqueous fluid, and wherein the method further comprises oxidation of the at least one organic compound in the aqueous fluid.

7. A method of producing methane comprising:
introducing a produced water comprising a chemical oxygen demand comprising at least one of a kinetic hydrate inhibitor and a hydrolyzed polyacrylamide to a treatment vessel;
subjecting the produced water to a pressure from about 20 atm to about 240 atm in or upstream of the treatment vessel;
subjecting the produced water to a temperature from about 150° C. to about 373° C. in or upstream of the treatment vessel;
introducing a heterogeneous catalyst to the produced water in or upstream of the treatment vessel to promote methane formation, wherein the heterogeneous catalyst comprises a member selected from the group consisting of ruthenium, nickel, cobalt, iron, and combinations thereof, and a solid support selected from the group consisting of alumina, silica, and a carbide; and
capturing the formed methane.

8. The method of claim 7, and wherein the chemical oxygen demand comprises at least 30,000 mg/L.

9. The method of claim 7, wherein the heterogeneous catalyst comprises ruthenium.

10. The method of claim 7, wherein introducing the catalyst facilitates hydrolysis of at least a portion of the constituents contributing to the chemical oxygen demand.

11. A method of producing methane comprising:
subjecting an aqueous fluid comprising at least one organic compound comprising at least one of a kinetic hydrate inhibitor and a hydrolyzed polyacrylamide to catalytic conditions effective to hydrolyze the at least one organic compound in the fluid and generate an amount of methane.

12. The method of claim 11, wherein the subjecting is done at a pressure of from about 20 atm to about 240 atm and at a temperature of from 150° C. to about 373° C.

13. The method of claim 11, wherein the aqueous fluid comprises produced water.

14. The method of claim 11, wherein the catalytic conditions comprise contact of the aqueous fluid with a heterogeneous catalyst, and wherein the heterogeneous catalyst includes a solid support selected from the group consisting of alumina, silica, and a carbide.

15. The method of claim 14, wherein the heterogeneous catalyst comprises a member selected from the group consisting of ruthenium, nickel, cobalt, iron, and combinations thereof.

16. The method of claim 11, wherein the heterogeneous catalyst comprises ruthenium.

17. The method of claim 11, wherein the subjecting is done in a treatment vessel, wherein the catalytic conditions further comprise introducing a pressurized oxygen-rich gas to the aqueous fluid, and wherein the catalytic conditions further facilitate oxidation of the at least one organic compound in the aqueous fluid.

* * * * *